(12) United States Patent
Kamada

(10) Patent No.: US 11,337,624 B2
(45) Date of Patent: May 24, 2022

(54) CONCENTRATION MEASUREMENT DEVICE AND CONCENTRATION MEASUREMENT METHOD

(71) Applicant: HAMAMATSU PHOTONICS K.K., Hamamatsu (JP)

(72) Inventor: Tsuyoshi Kamada, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 363 days.

(21) Appl. No.: 16/331,202

(22) PCT Filed: Sep. 4, 2017

(86) PCT No.: PCT/JP2017/031823
§ 371 (c)(1),
(2) Date: Mar. 7, 2019

(87) PCT Pub. No.: WO2018/051832
PCT Pub. Date: Mar. 22, 2018

(65) Prior Publication Data
US 2019/0274605 A1    Sep. 12, 2019

(30) Foreign Application Priority Data

Sep. 14, 2016 (JP) .............................. JP2016-179424

(51) Int. Cl.
*A61B 5/1455* (2006.01)
*A61B 5/145* (2006.01)
(Continued)

(52) U.S. Cl.
CPC ........ *A61B 5/14535* (2013.01); *A61B 5/1455* (2013.01); *A61B 5/6814* (2013.01); *A61H 31/00* (2013.01); *G01N 21/27* (2013.01)

(58) Field of Classification Search
CPC . A61B 5/0205; A61B 5/1455; A61B 5/14551; A61B 5/14552; A61B 5/14535;
(Continued)

(56) References Cited

U.S. PATENT DOCUMENTS 5,997,343 A  * 12/1999 Mills .................. A61B 5/14552
439/489
8,265,723 B1 *  9/2012 McHale ............. A61B 5/14552
600/310
(Continued)

FOREIGN PATENT DOCUMENTS

CN         103349815 A      10/2013
CN         103735401 A       4/2014
(Continued)

OTHER PUBLICATIONS

International Preliminary Report on Patentability dated Mar. 28, 2019 for PCT/JP2017/031823.

*Primary Examiner* — Chu Chuan Liu
(74) *Attorney, Agent, or Firm* — Faegre Drinker Biddle & Reath LLP

(57) ABSTRACT

A concentration measurement apparatus includes a probe being attached to a head and having a light source for outputting measurement light and a photodetection unit for generating a detection signal according to an intensity of incident light, a calculation unit for performing a calculation of a hemoglobin concentration-related numerical value in the head which varies due to repetition of chest compression on the basis of the detection signal according to the intensity of the measurement light propagated through the inside of the head, and an instruction unit for instructing the calculation unit to start the calculation. The photodetection unit continuously generates the detection signal before the calculation start in the calculation unit. The instruction unit
(Continued)

determines the calculation start on the basis of the detection signal.

8 Claims, 6 Drawing Sheets

(51) Int. Cl.
    *A61B 5/00*     (2006.01)
    *G01N 21/27*     (2006.01)
    *A61H 31/00*     (2006.01)

(58) Field of Classification Search
CPC . A61B 5/14553; A61B 5/4836; A61B 5/6814; A61B 5/6844
See application file for complete search history.

(56) References Cited

U.S. PATENT DOCUMENTS

| | | | |
|---|---|---|---|
| 9,339,240 | B2 | 5/2016 | Widman et al. |
| 2004/0267324 | A1 | 12/2004 | Geheb et al. |
| 2012/0286955 | A1* | 11/2012 | Welch ............... A61B 5/14551 340/573.1 |
| 2014/0058233 | A1* | 2/2014 | Koyama ............ A61B 5/14551 600/328 |
| 2014/0142403 | A1 | 5/2014 | Brumback et al. |
| 2015/0105636 | A1 | 4/2015 | Hayman et al. |
| 2015/0208962 | A1 | 7/2015 | Baker, Jr. |
| 2016/0206504 | A1 | 7/2016 | Giarracco et al. |

FOREIGN PATENT DOCUMENTS

| | | |
|---|---|---|
| CN | 105078422 A | 11/2015 |
| CN | 105164627 A | 12/2015 |
| CN | 105491987 A | 4/2016 |
| CN | 105748059 A | 7/2016 |
| JP | H06-319723 A | 11/1994 |
| JP | 2001-190503 A | 7/2001 |
| JP | 2012-65707 A | 4/2012 |
| JP | 2012-223451 A | 11/2012 |
| JP | 2013-169280 A | 9/2013 |
| JP | 2013-170881 A | 9/2013 |
| JP | 2016-000240 A | 1/2016 |
| TW | 201347735 A | 12/2013 |

* cited by examiner

CONCENTRATION MEASUREMENT DEVICE AND CONCENTRATION MEASUREMENT METHOD

TECHNICAL FIELD

The present disclosure relates to a concentration measurement apparatus and a concentration measurement method.

BACKGROUND ART

As apparatuses for noninvasively measuring information on a hemoglobin concentration in a living body, there are apparatuses, for example, disclosed in Patent Documents 1 to 3. In these apparatuses, after light is incident on the inside of the living body, light scattered in the living body is detected in each of a plurality of photodiodes. Then, on the basis of the intensities of the detected light, hemoglobin oxygen saturation, and respective concentration changes of oxygenated hemoglobin ($O_2Hb$), deoxygenated hemoglobin (HHb), and total hemoglobin (cHb) are calculated.

CITATION LIST

Patent Literature

Patent Document 1: Japanese Patent Application Laid-Open Publication No. 2012-223451
Patent Document 2: Japanese Patent Application Laid-Open Publication No. 2013-169280
Patent Document 3: Japanese Patent Application Laid-Open Publication No. 2013-170881

SUMMARY OF INVENTION

Technical Problem

The primary patients in the emergency life-saving field in recent years are cardiopulmonary arrest persons outside hospitals. There are more than 100,000 persons in cardiopulmonary arrest outside hospitals per year, and the life-saving of these patients is a great social demand. An essential treatment for a cardiopulmonary arrest person outside a hospital is chest compression performed in combination with artificial respiration. The chest compression is an act of giving artificial heartbeats to the stopped heart by periodically compressing the lower half of the breastbone with hands of another person. The main purpose of the chest compression is to supply blood oxygen to the brain of the cardiopulmonary arrest person. Therefore, whether the chest compression is appropriately performed greatly influences the life and death of the cardiopulmonary arrest person. Thus, it is desirable to objectively determine whether the chest compression is appropriately performed on the basis of, for example, a hemoglobin concentration or the like in the head.

However, during a time-sensitive treatment for the cardiopulmonary arrest person, there is almost no room for performing an operation such as a start of the measurement in the measurement apparatus in order to measure the hemoglobin concentration or the like in the head. On the other hand, it may become difficult to perform accurate measurement in the measurement apparatus unless the timing of the start of the measurement is appropriate.

It is an object of an embodiment to provide a concentration measurement apparatus and a concentration measurement method capable of automatically determining appropriate timing of the start of the measurement.

Solution to Problem

An embodiment of the present invention is a concentration measurement apparatus. The concentration measurement apparatus is an apparatus for measuring a hemoglobin concentration-related numerical value in a head which varies due to repetition of chest compression, and the concentration measurement apparatus includes a probe including a light source for outputting measurement light and a photodetection unit for generating a detection signal according to an intensity of incident light, the probe being attached to the head, a calculation unit electrically coupled to the probe, and for performing a calculation of the hemoglobin concentration-related numerical value in the head which varies due to the repetition of chest compression on the basis of the detection signal according to the intensity of the measurement light propagated through the inside of the head, and an instruction unit for instructing the calculation unit to start the calculation, and the photodetection unit continuously generates the detection signal before the start of the calculation in the calculation unit, and the instruction unit determines the start of the calculation on the basis of the detection signal.

An embodiment of the present invention is a concentration measurement method. The concentration measurement method is a method of measuring a hemoglobin concentration-related numerical value in a head, with a probe attached thereto, which varies due to repetition of chest compression, the probe including a light source for outputting measurement light and a photodetection unit for generating a detection signal according to an intensity of incident light, and the concentration measurement method includes a step of starting the generation of the detection signal in the photodetection unit, a step of determining a start of a calculation of the hemoglobin concentration-related numerical value in the head which varies due to the repetition of chest compression on the basis of the detection signal, and a step of outputting the measurement light from the light source, and performing the calculation of the hemoglobin concentration-related numerical value on the basis of the detection signal according to the intensity of the measurement light propagated through the inside of the head.

In the above concentration measurement apparatus and the concentration measurement method, the photodetection unit continuously generates the detection signal before the start of the calculation of the numerical value related to hemoglobin concentration. Then, the start of the calculation of the hemoglobin concentration-related numerical value is determined on the basis of the detection signal continuously generated before the start of the calculation. Before the probe is attached to the head, the incident intensity of surrounding light (ambient light) on the photodetection unit is large, but when the probe is attached to the head, the incident intensity of the ambient light decreases. Therefore, on the basis of, for example, a change in the detection signal due to such a change in the intensity of the ambient light (the detection signal is a predetermined value or less), it is possible to appropriately and automatically determine that the probe is attached to the head, that is, the timing of the start of the calculation (start of the measurement).

Advantageous Effects of Invention

According to the embodiment, it is possible to provide a concentration measurement apparatus and a concentration measurement method capable of automatically determining appropriate timing of the start of the measurement.

BRIEF DESCRIPTION OF DRAWINGS

FIG. 4 is a flowchart illustrating in detail steps of calculating a hemoglobin concentration or the like.

DESCRIPTION OF EMBODIMENTS

Hereinafter, embodiments of a concentration measurement apparatus and a concentration measurement method will be described in detail with reference to the accompanying drawings. In the description of the drawings, the same elements will be denoted by the same reference signs, and overlapping description will be omitted.

Embodiment

Figure 1:
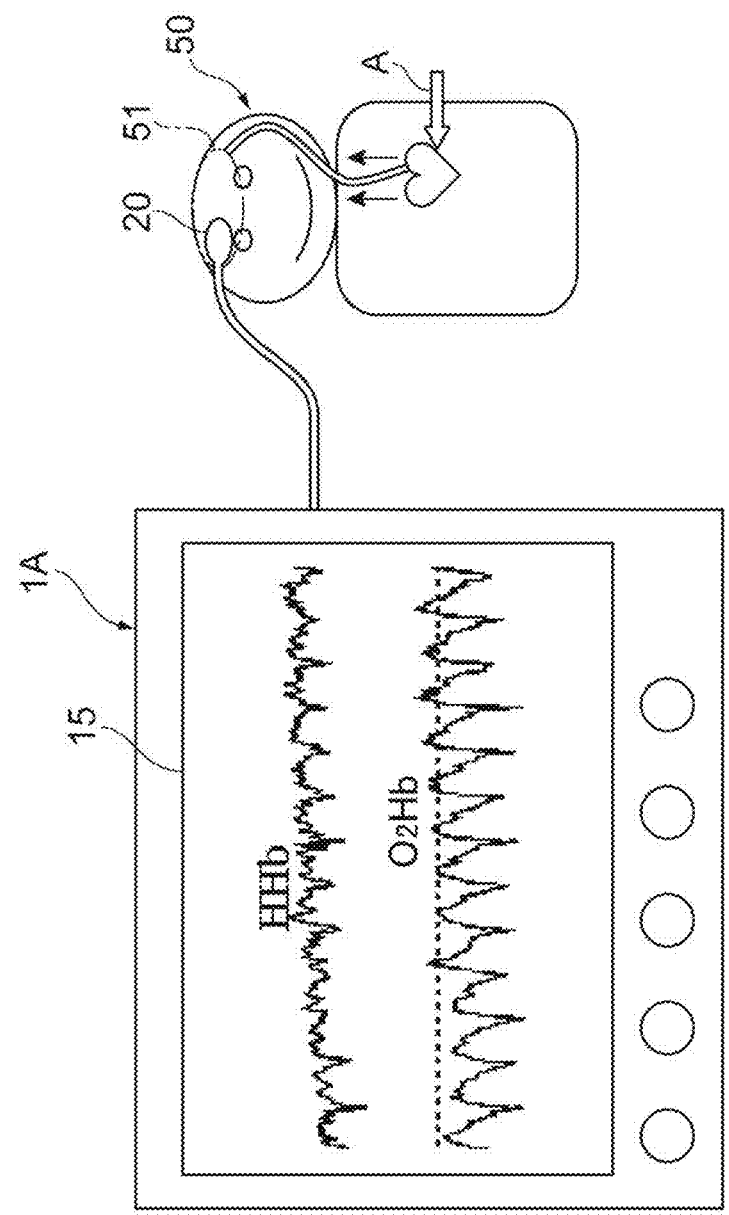
FIG. 1 is a conceptual diagram of a concentration measurement apparatus according to an embodiment.

FIG. 1 is a conceptual diagram of a concentration measurement apparatus 1A according to an embodiment. This concentration measurement apparatus 1A is mainly used at an emergency medical care site and the like, and measures a hemoglobin concentration or a hemoglobin concentration-related numerical value in a head 51, which varies due to repetition of chest compression, for providing objective information for determination as to whether the chest compression (arrow A in the figure) to a cardiopulmonary arrest person 50 is appropriately performed. Further, a measurement result is displayed on a display unit 15 to notify a person performing the chest compression.

Here, the "hemoglobin concentration" specifically refers to at least one of a total hemoglobin (cHb) concentration, an oxygenated hemoglobin ($O_2Hb$) concentration, and a deoxygenated hemoglobin (HHb) concentration. Further, the "hemoglobin concentration-related numerical value" refers to a parameter of, for example, "hemoglobin concentration", a temporal variation (relative change amount) from an initial amount at a certain reference time point, a concentration (absolute amount) of each of cHb, $O_2Hb$, and HHb at a measurement time, a ratio of a concentration or a concentration change amount among cHb, $O_2Hb$, and HHb, or oxygen saturation, or a cycle of a temporal change in "hemoglobin concentration". In the following description, the "hemoglobin concentration-related numerical value" is referred to as "hemoglobin concentration or the like".

The concentration measurement apparatus 1A causes measurement light of a predetermined wavelength to be incident on a predetermined light incident position from a probe 20 attached (for example, affixed) to the head 51, and detects the intensity of the measurement light emitted from a predetermined light detection position on the head 51, thereby examining influence of oxygenated hemoglobin ($O_2Hb$) and deoxygenated hemoglobin (HHb) on the measurement light and repeatedly calculating information such as concentrations of oxygenated hemoglobin ($O_2Hb$) and deoxygenated hemoglobin (HHb), on the basis of the result. Further, filter processing is applied to the time-series data that is a result of the calculation, and low frequency components are removed, whereby a temporal variation component of a short cycle due to repetition of chest compression is extracted and the temporal variation component is displayed in a visible manner.

Figure 2:
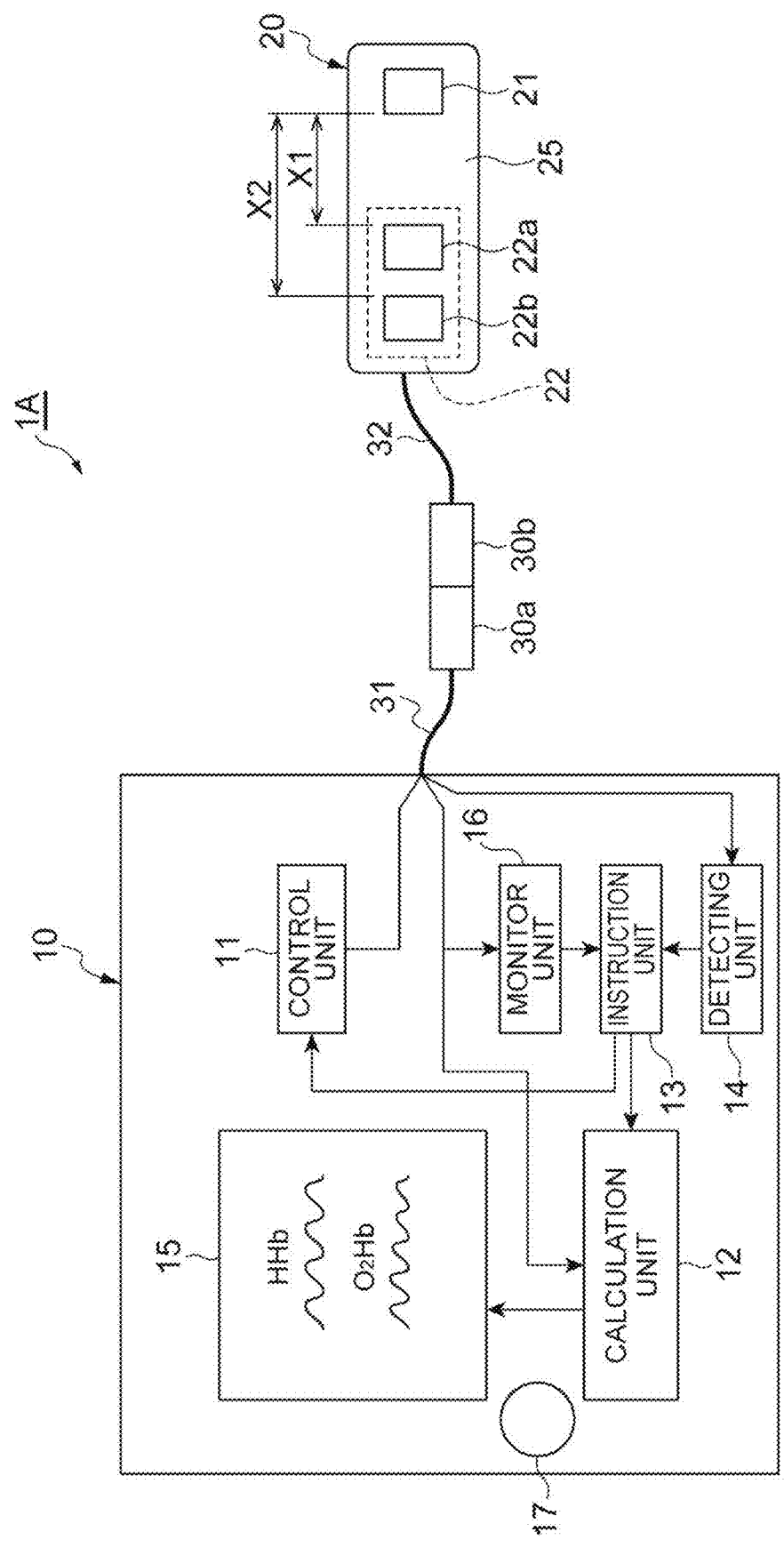
FIG. 2 is a diagram illustrating a specific configuration example of the concentration measurement apparatus.

FIG. 2 is a diagram illustrating a specific configuration example of the concentration measurement apparatus 1A. The concentration measurement apparatus 1A includes a main unit 10 and a probe 20. The probe 20 is fixed, for example, by an adhesive tape, a stretchable band or the like to a vicinity of a forehead without hair or a carotid artery. The probe 20 has a light source 21 and a photodetection unit 22. The light source 21 and the photodetection unit 22 are disposed while being spaced from each other and are substantially integrated by a flexible black silicon rubber holder 25.

The probe 20 is electrically coupled to the main unit 10. Specifically, the probe 20 is electrically connected to a connector 30b via a cable 32. The connector 30b is connected in an attachable and detachable manner to a connector 30a on a side of the main unit 10. The connector 30a is electrically connected to the main unit 10 via a cable 31.

The light source 21 receives a control signal transmitted from the main unit 10 of the concentration measurement apparatus 1A and outputs measurement light of a predetermined wavelength. The measurement light is incident nearly perpendicularly on a skin layer of the head 51. The light source 21 includes, for example, a laser diode, a light emitting diode (LED), or a super luminescent diode (SLD), and a driving circuit for the diode. The measurement light is, for example, near infrared light, and in one example, includes wavelength components of 735 nm, 810 nm, and 850 nm.

The photodetection unit 22 generates a detection signal according to the intensity of the incident light. In particular, when the hemoglobin concentration or the like is calculated, the photodetection unit 22 detects the measurement light propagated through the inside of the head 51 and generates the detection signal according to the intensity of the measurement light. The photodetection unit 22 is, for example, a one-dimensional light sensor and includes a plurality of photodetectors arranged in a direction of a distance from the light source 21. The photodetection unit 22 according to the present embodiment includes two photodetectors of a first photodetector 22a and a second photodetector 22b. The first photodetector 22a is provided at a position separated from the light source 21 by a first distance X1. The second photodetector 22b is provided at a position separated from the light source 21 by a second distance X2 (>X1). The distance X1 is, for example, 3 cm, and the distance X2 is, for example, 4 cm.

The first photodetector 22a generates a first detection signal according to the intensity of the incident light. The second photodetector 22b generates a second detection signal according to the intensity of the incident light. These photodetectors 22a and 22b each includes a semiconductor light receiving element such as a PD (photodiode) or an APD (avalanche photodiode), and a preamplifier that integrates and amplifies a current output from the semiconductor light receiving element. As a result, the photodetectors 22a and 22b can detect a weak current with good sensitivity, generate a detection signal, and transmit this detection signal to the main unit 10 via the cables 31 and 32. Further, the photodetection unit 22 may be a two-dimensional light sensor, and may include, for example, a CCD image sensor or a CMOS image sensor.

The main unit (controller) 10 includes a control unit 11, a calculation unit 12 that calculates the hemoglobin concentration or the like, an instruction unit 13 that instructs the calculation unit 12 to start the calculation, a detecting unit 14, the display unit 15, a monitor unit 16, and a speaker 17. The main unit 10 includes an arithmetic circuit such as a CPU and a storage device such as a memory. The main unit 10 may include a personal computer or a smart device such as a smartphone or a tablet terminal. Further, the main unit 10 may include a cloud server, and in this case, at least one function of the control unit 11, the calculation unit 12, and the instruction unit 13 may be achieved by the cloud server.

The control unit 11 is electrically coupled to the probe 20 via the cables 31 and 32. The control unit 11 performs light output control of the light source 21 and light detection control of the photodetectors 22a and 22b. That is, the start and end of output of the measurement light in the light source 21 are performed on the basis of the control signal from the control unit 11. Similarly, the start and end of detection of the measurement light in the photodetectors 22a and 22b are performed on the basis of the control signal from the control unit 11.

The detecting unit 14 detects that the connector 30a and the connector 30b are connected to each other. The detecting unit 14 may be a touch sensor built in the connector 30a or may have a detecting circuit that detects an electric signal generated by the connection. When the detecting unit 14 detects the connection of the connector 30a and the connector 30b, the control unit 11 of the present embodiment outputs a detecting signal to the instruction unit 13. When the instruction unit 13 receives the detecting signal, the instruction unit causes the photodetectors 22a and 22b to start the detection of the measurement light (standby mode). The standby mode continues until the calculation unit 12 starts the calculation of the hemoglobin concentration or the like, and the calculation unit 12 does not perform the calculation of the hemoglobin concentration or the like in the standby mode.

The monitor unit 16 monitors (observes) changes in the intensities of light incident on the photodetectors 22a and 22b on the basis of the detection signals from the photodetection unit 22 that are continuously generated before the start of the calculation in the calculation unit 12, that is, in the standby mode. The monitor unit 16 continuously outputs a result of the monitoring to the instruction unit 13.

On the basis of the result of the monitoring obtained from the monitor unit 16, the instruction unit 13 determines the start of the calculation of the hemoglobin concentration or the like, and instructs the calculation unit 12 to start the calculation (measurement mode). The detection signal from each of the photodetectors 22a and 22b at the start of the standby mode indicates the light intensity before the probe 20 is attached to the head 51, that is, the intensity of ambient light in a measurement environment (for example, sunlight for outdoors, illumination light for indoors). Then, when the probe 20 is attached to the head 51, the intensity of the ambient light decreases to a predetermined proportion (for example, 10%) or less with respect to the intensity before the attachment. The instruction unit 13 can know such a decrease in the intensity depending on whether the intensity of the measurement light detected by the photodetectors 22a and 22b has changed to be within a predetermined range. Therefore, the instruction unit 13 may determine the start of the calculation on the condition that the intensity of the measurement light detected by the photodetectors 22a and 22b is within a predetermined range.

Here, even before the probe 20 is attached to the head, when the probe 20 is handled by a performer, the detection intensity of the ambient light may decrease, for example, by covering the photodetection unit 22 with a hand or the like. Therefore, the instruction unit 13 may determine the start of the calculation on the condition that a state in which the intensity of the measurement light detected by the photodetection unit 22 is within the predetermined range continues for a predetermined period (for example, three seconds).

In addition, the instruction unit 13 may determine the start of the calculation on the condition that a change in intensity of the measurement light detected by the photodetectors 22a and 22b has exceeded a predetermined width.

Further, the instruction unit 13 may also determine the start of the calculation on the basis of the light intensity detected by the second photodetector 22b that is the farthest from the light source among the two photodetectors 22a and 22b. As a result, the change in the incident light intensity (ambient light intensity) can be obtained more accurately, and timing at which the probe 20 is attached to the head 51 can be accurately detected.

The calculation unit 12 is a calculation processing circuit electrically coupled to the probe 20 via the cables 31 and 32. On the basis of the detection signal from the photodetection unit 22 according to the intensity of the measurement light propagated through the inside of the head 51, the calculation unit 12 calculates the hemoglobin concentration or the like in the head 51, which varies due to repetition of chest compression. When the calculation unit 12 receives an instruction from the instruction unit 13 to be described later, the calculation unit starts the calculation of the hemoglobin concentration or the like.

The calculation unit 12 calculates the hemoglobin concentration or the like by using a near-infrared spectroscopic method, for example, a SRS method (spatially resolved spectroscopy method), a MBL method (modified Beer Lambert method), a PRS method (phase resolved spectroscopy method), a TRS method (time resolved spectroscopy method), a PMS method (phase modulation spectroscopy method).

The MBL method uses the fact that an amount of light detected changes according to a hemoglobin concentration (oxygenated hemoglobin concentration and deoxygenated hemoglobin concentration) in a measurement object. By the MBL method, a relative change amount of the oxygenated hemoglobin concentration, a relative change amount of the deoxygenated hemoglobin concentration, and a relative change amount of a total hemoglobin concentration can be obtained. In the MBL method, a detection signal from one of the photodetectors 22a and 22b is used.

The SRS method uses the fact that the amount of light detected changes according to distances between the light source 21 and the photodetectors 22a and 22b. By the SRS method, oxygen saturation (TOI) that is a proportion of an oxygenated hemoglobin concentration to a total hemoglobin concentration, and a relative value of the total hemoglobin concentration can be obtained. In the SRS method, detection signals from both the photodetectors 22a and 22b are used.

The TRS method uses the fact that the time width of input pulsed measurement light becomes longer due to hemoglobin present in a measurement object. More specifically, an absolute value of the hemoglobin concentration is obtained by fitting simulation data based on a temporal spread of the pulsed measurement light and a temporal spread of the detected light.

In the PRS method, modulated measurement light is incident on a measurement object, and an absolute value of the hemoglobin concentration is obtained by obtaining a phase difference between measurement light before incidence and measurement light after detection.

Further, the calculation unit 12 may perform filter processing on the time-series data of the calculated hemoglobin concentration or the like and removes frequency components less than a predetermined frequency among frequency components included in the time-series data, thereby extracting the temporal variation component due to repetition of chest compression. Here, "filter processing of removing frequency components less than a predetermined frequency" refers to processing of reducing a proportion of frequency components less than the predetermined frequency until the frequency component due to the chest compression appears at a sufficiently distinguishable level, and the processing is not limited to processing of completely removing the frequency components less than the predetermined frequency.

Further, it is preferable that the calculation cycle of the hemoglobin concentration or the like is 0.2 seconds or less (5 Hz or more in terms of a calculation frequency). In general, a preferred cycle of the chest compression is said to be about 100 times per minute (that is, once every 0.6 seconds) or more. Then, when the calculation cycle of the relative change amount is one third or less of the above cycle, it is possible to suitably detect a concentration change due to the chest compression. Further, it is preferable that the predetermined frequency described above is 1.66 Hz or less. As a result, it is possible to suitably extract information on the concentration change due to the chest compression about 100 times or more per minute.

The display unit 15 displays information on the calculation result of the hemoglobin concentration or the like sent from the calculation unit 12. While referring to the display on the display unit 15, the performer determines whether the chest compression is appropriately performed. Further, a speaker (attention calling unit) 17 outputs, by sound, information prompting the performer of the chest compression to change the speed of the chest compression and to change the intensity of the chest compression.

Figure 3:
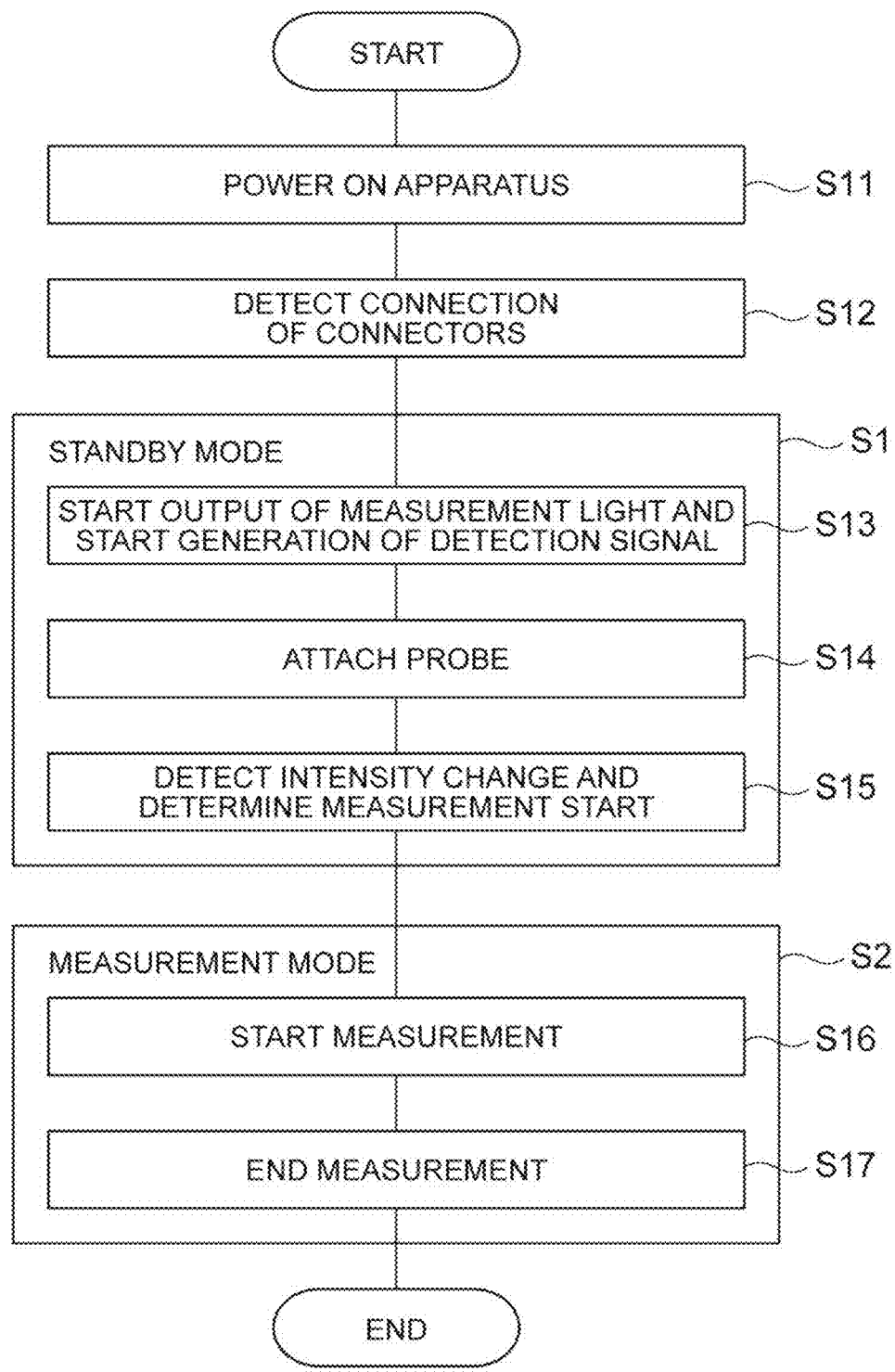
FIG. 3 is a flowchart illustrating an operation of the concentration measurement apparatus and a concentration measurement method.

Subsequently, the concentration measurement method according to the present embodiment will be described together with the operation of the concentration measurement apparatus 1A. FIG. 3 is a flowchart illustrating the operation of the concentration measurement apparatus 1A and the concentration measurement method according to the present embodiment. In this concentration measurement method, similarly to the concentration measurement apparatus 1A, the hemoglobin concentration or the like (hemoglobin concentration-related value) in the head 51, which varies due to repetition of chest compression, is measured.

First, the performer of the chest compression powers on the concentration measurement apparatus 1A (step S11). As a result, the detecting unit 14 starts operation for detecting that the connectors 30a and 30b are connected.

Next, the performer of the chest compression connects the connector 30a and the connector 30b. As a result, the main unit 10 and the probe 20 are electrically coupled to each other. At this time, the detecting unit 14 detects that the connectors 30a and 30b are connected, and the detecting unit 14 outputs a detecting signal to the instruction unit 13 (step S12). The instruction unit 13 instructs the control unit 11 and the calculation unit 12 to perform the standby mode S1. The control unit 11 starts the output of the measurement light from the light source 21 and the generation of a detection signal in the photodetection unit 22 (step S13). Further, the monitor unit 16 starts the monitoring of the light intensity incident on the photodetectors 22a and 22b.

Here, in step S12, the detecting unit 14 detects that the connectors 30a and 30b are connected, whereby the concentration measurement apparatus 1A may be powered on automatically. In this case, step S11 described above is unnecessary. Further, steps S11 and S12 described above may be performed before the performer arrives at a place of the cardiopulmonary arrest person (emergency site) or may be performed after the performer arrives there.

Subsequently, the performer attaches the probe 20 to the head of the cardiopulmonary arrest person (step S14). At this time, since the intensity of the ambient light incident on the photodetection unit 22 decreases, the instruction unit 13 determines the start of the calculation of the hemoglobin concentration or the like on the basis of the result of the monitoring from the monitor unit 16 (step S15). That is, the instruction unit 13 instructs the control unit 11 and the calculation unit 12 to perform the measurement mode S2. As described above, in this step, the start of the calculation may be determined on the condition that the intensity of the measurement light detected by the photodetection unit 22 is within the predetermined range, or the start of the calculation may be determined on the condition that the state in which the intensity of the measurement light detected by the photodetection unit 22 is within the predetermined range continues for the predetermined period. Further, as described above, it is preferable to determine the start of the calculation on the basis of the light intensity detected by the photodetector 22b far from the light source 21.

Subsequently, according to the instruction from the instruction unit 13, the control unit 11 starts the output of the measurement light from the light source 21. At this time, the photodetection unit 22 continues from the standby mode S to generate the detection signal. Further, the calculation unit 12 starts the calculation of the hemoglobin concentration or the like on the basis of the detection signal according to the intensity of the measurement light propagated through the inside of the head (step S16). Thereafter, measurement is completed by input from the performer (step S17).

Figure 4:
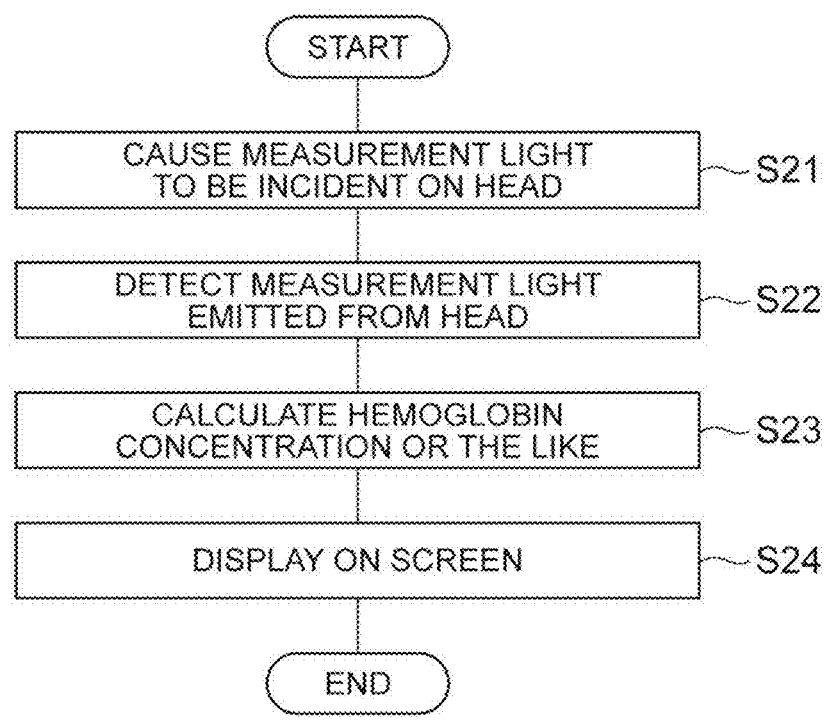

FIG. 4 is a flowchart illustrating in detail steps of calculating the hemoglobin concentration or the like. First, the light source 21 outputs the measurement light of a predetermined wavelength on the basis of the control signal from the control unit 11. The measurement light is incident on the head from the predetermined light incident position (step S21). The measurement light incident into the head is scattered inside the head and propagates while being absorbed by a component to be measured, and a part of the light reaches the light detection position of the head. The measurement light having reached the light detection position is detected by the photodetection unit 22 (step S22). The photodetection unit 22 generates the detection signal according to the intensity of the detected measurement light.

Subsequently, the calculation unit 12 calculates the hemoglobin concentration or the like on the basis of the detection signal (step S23). As described above, various near-infrared spectroscopic methods such as the SRS method, the MBL method, the PRS method, and the TRS method can be used as a calculation method. Information on the calculated hemoglobin concentration or the like is displayed on the display unit 15 (step S24). In the step of calculating the hemoglobin concentration or the like, steps S21 to S24 described above are repeated.

Effects obtained by the concentration measurement apparatus 1A and the concentration measurement method according to the embodiment described above will be described. Recently, in the evaluation of chest compression, the effectiveness of measuring a hemoglobin concentration or the like in a head has been recognized. However, there is a need for an apparatus capable of starting the measurement more easily from emergency medical care sites. In conventional apparatuses, it is necessary to perform an operation for starting the measurement before performing the chest compression, and there is a demand to omit time required for the operation. Further, considering the storage of measurement data and the safety of light emitted from the light source 21, it is desirable to start the measurement of the hemoglobin concentration or the like after the probe 20 is attached to the head.

In the present embodiment, the photodetection unit 22 continuously generates the detection signal before the start of the calculation of the hemoglobin concentration or the like. Then, on the basis of the detection signal continuously generated before the start of the calculation, the start of the calculation of the hemoglobin concentration or the like is determined. As described above, before the probe 20 is attached to the head, the incident intensity of surrounding light (ambient light) on the photodetection unit 22 is large, but when the probe 20 is attached to the head, the incident intensity of the ambient light decreases. Therefore, on the basis of a change in the detection signal due to such a change in the intensity of the ambient light (specifically, the detection signal is a predetermined value or less) or the like, it is possible to appropriately and automatically determine that the probe 20 is attached to the head, that is, the timing of the start of the calculation (start of the measurement).

Further, as in the present embodiment, in the instruction unit 13 or step S15, the start of the calculation may be determined on the condition that the intensity of the incident light on the photodetection unit 22 is within a predetermined range. In addition, the start of the calculation may be determined on the condition that a state in which the intensity of the incident light on the photodetection unit 22 is within a predetermined range continues for a predetermined period. For example, by determining the start of the calculation of the hemoglobin concentration or the like on the basis of these conditions, it is possible to appropriately determine the timing of the start of the calculation (start of the measurement).

(First Modification)

Figure 5:
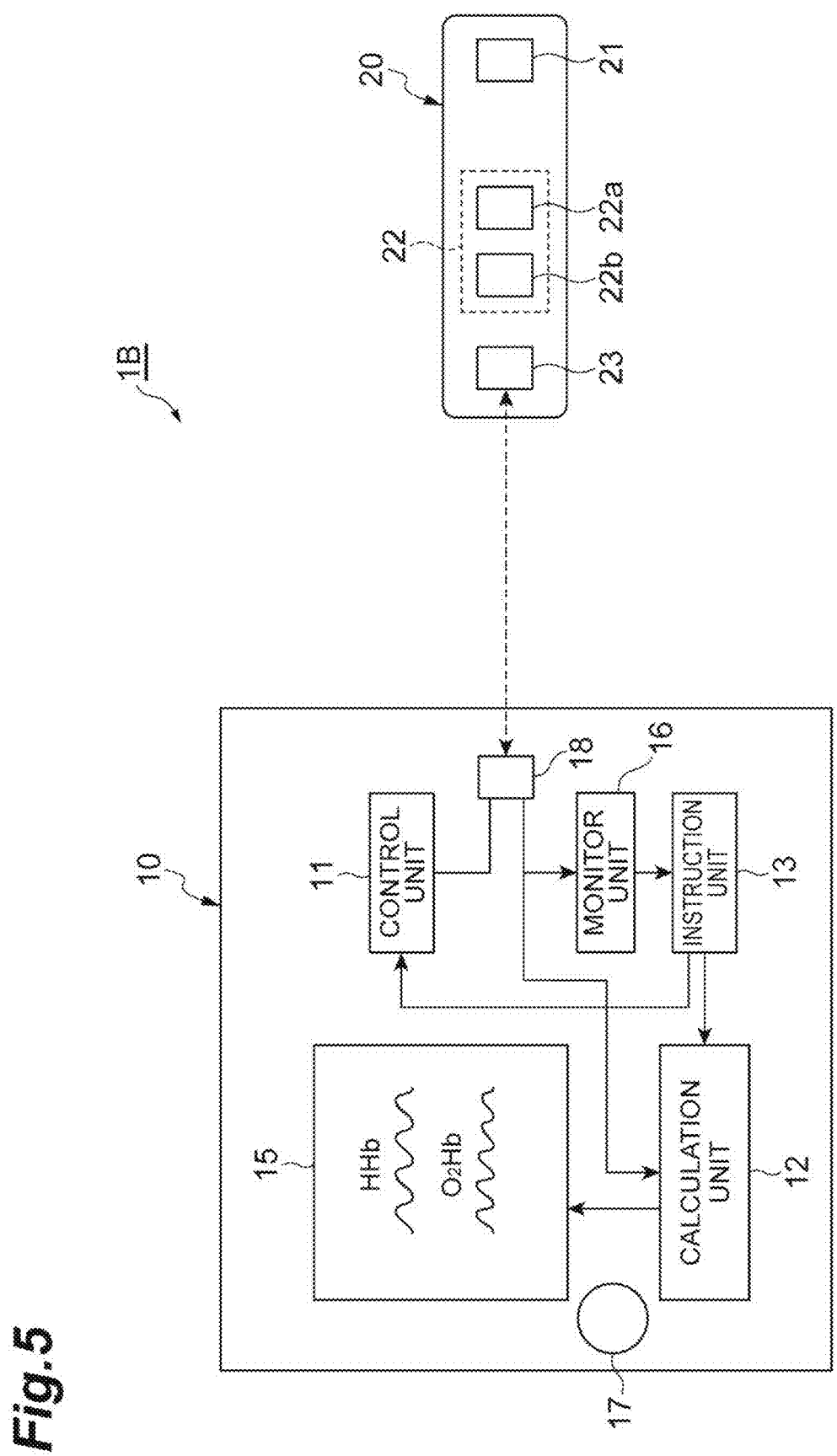
FIG. 5 is a diagram illustrating a configuration of a concentration measurement apparatus according to a first modification.

FIG. 5 is a diagram illustrating a configuration of a concentration measurement apparatus 1B according to a first modification of the above embodiment. A difference from the above embodiment is connecting means between the main unit 10 and the probe 20. Instead of the cables 31 and 32 and the connectors 30a and 30b of the above embodiment, the concentration measurement apparatus 1B according to the present modification includes transmitting-receiving devices 18 and 23 as wireless means. The transmitting-receiving device 18 is included in the main unit 10, and the transmitting-receiving device 23 is included in the probe 20. The transmitting-receiving device 18 transmits the control signal from the control unit 11 and the instruction on the standby mode from the instruction unit 13 to the transmitting-receiving device 23. The transmitting-receiving device 23 transmits the received control signal and the instruction respectively to the light source 21 and the photodetection unit 22. Further, the transmitting-receiving device 23 transmits the detection signal from the photodetection unit 22 to the transmitting-receiving device 18. The transmitting-receiving device 18 transmits the received detection signal to the calculation unit 12 and the instruction unit 13.

Even with the configuration of the present modification, the same effects as those of the above embodiment can be suitably obtained. As the connecting means between the main unit 10 and the probe 20, various means can be applied without being limited to the above embodiment and the present modification.

(Second Modification)

Figure 6:
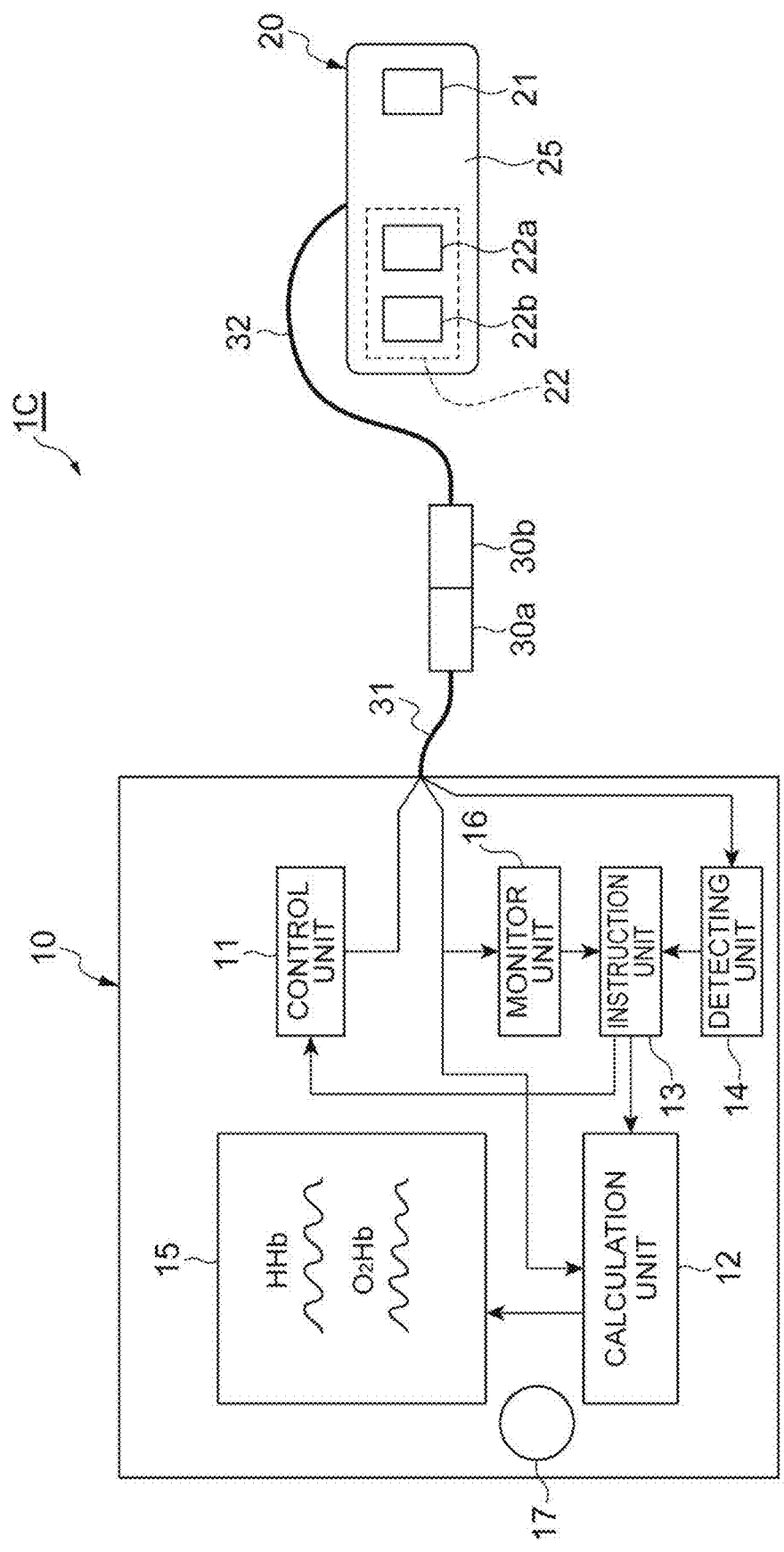
FIG. 6 is a diagram illustrating a configuration of a concentration measurement apparatus according to a second modification.

FIG. 6 is a diagram illustrating a configuration of a concentration measurement apparatus 1C according to a second modification of the above embodiment. In the above embodiment, the cable 32 extends from one end of the probe 20 (see FIG. 2), but as in the present modification, the cable 32 may extend from a center portion of the probe 20.

(Third Modification)

In the above embodiment, a case where the probe 20 is attached to the head of the cardiopulmonary arrest person after the performer connects the connectors 30a and 30b has been described, but a case where the connectors 30a and 30b are connected after the probe 20 is attached to the head is also assumed. In this case, since ambient light incident on the photodetection unit 22 has already decreased, no change in incident light intensity occurs. Therefore, the instruction unit 13 may determine the start of the calculation of the hemoglobin concentration or the like even in the case where a change in an incident light intensity does not occur for a predetermined time (for example, three seconds) after the start of the standby mode.

The concentration measurement apparatus and the concentration measurement method are not limited to the embodiments described above, and various other modifications are possible. For example, the above respective embodiments may be combined with each other according to necessary purposes and effects.

The concentration measurement apparatus according to the above embodiment is a concentration measurement apparatus for measuring a hemoglobin concentration-related numerical value in a head which varies due to repetition of chest compression, and the apparatus is configured to include a probe including a light source for outputting measurement light and a photodetection unit for generating a detection signal according to an intensity of incident light, the probe being attached to the head, a calculation unit electrically coupled to the probe, and for performing a calculation of the hemoglobin concentration-related numerical value in the head which varies due to the repetition of chest compression on the basis of the detection signal according to the intensity of the measurement light propagated through the inside of the head, and an instruction unit for instructing the calculation unit to start the calculation, and the photodetection unit continuously generates the detection signal before the start of the calculation in the calculation unit, and the instruction unit determines the start of the calculation on the basis of the detection signal.

The concentration measurement method according to the above embodiment is a concentration measurement method of measuring a hemoglobin concentration-related numerical value in a head, with a probe applied thereto, which varies due to repetition of chest compression, the probe including a light source for outputting measurement light and a photodetection unit for generating a detection signal according to an intensity of incident light, and the method is configured to include a step of starting the generation of the detection signal in the photodetection unit, a step of determining a start of a calculation of the hemoglobin concentration-related numerical value in the head which varies due to the repetition of chest compression on the basis of the detection signal, and a step of outputting the measurement light from the light source, and performing the calculation of the hemoglobin concentration-related numerical value on the basis of the detection signal according to the intensity of the measurement light propagated through the inside of the head.

In the above concentration measurement apparatus and the concentration measurement method, in the instruction unit or the step of determining the start of the calculation, the start of the calculation may be determined on the condition that the intensity of the incident light is within a predetermined range.

Further, in the above concentration measurement apparatus and the concentration measurement method, in the instruction unit or the step of determining the start of the calculation, the start of the calculation may be determined on the condition that a state in which the intensity of the incident light is within a predetermined range continues for a predetermined period.

For example, by determining the start of the calculation of the hemoglobin concentration-related numerical value on the basis of these conditions, it is possible to appropriately determine the timing of the start of the calculation (start of the measurement).

Further, in the above concentration measurement apparatus and the concentration measurement method, the photodetection unit may include a first photodetector separated from the light source by a first distance and a second photodetector separated from the light source by a second distance longer than the first distance, and in the instruction unit or the step of determining the start of the calculation, the start of the calculation may be determined on the basis of the intensity of the incident light on the second photodetector.

In this way, by determining the start of the calculation on the basis of the intensity of the measurement light detected by the photodetector far from the light source, a change in the intensity of the ambient light can be obtained more accurately.

INDUSTRIAL APPLICABILITY

An embodiment can be used as a concentration measurement apparatus and a concentration measurement method capable of automatically determining appropriate timing of the start of the measurement.

REFERENCE SIGNS LIST 1A, 1B, 1C—concentration measurement apparatus, 10—main unit, 11—control unit, 12—calculation unit, 13—instruction unit, 14—detecting unit, 15—display unit, 16—monitor unit, 17—speaker, 18, 23—transmitting-receiving device, 20—probe, 21—light source, 22—photodetection unit, 22a—first photodetector, 22b—second photodetector, 25—holder, 30a, 30b—connector, 31, 32—cable, 50—cardiopulmonary arrest person, 51—head.

The invention claimed is:

1. A concentration measurement apparatus for measuring a hemoglobin concentration-related numerical value in a head which varies due to repetition of chest compression, the concentration measurement apparatus comprising:
    a probe comprising a light source configured to output measurement light and a photodetection unit configured to generate a detection signal according to an intensity of incident light, the probe being attached to the head; and
    a controller electrically coupled to the probe, wherein the controller comprises:
        a calculation unit configured to perform a calculation of the hemoglobin concentration-related numerical value in the head which varies due to the repetition of chest compression on the basis of the detection signal according to the intensity of the measurement light propagated through the inside of the head;
        an instruction unit configured to instruct the calculation unit to start the calculation; and
        a detecting unit configured to detect a connection of the controller and the probe, wherein
        the detecting unit is configured to output a detecting signal to the instruction unit when the connection of the controller and the probe is detected, and the instruction unit is configured to cause the light source to start the output of the measurement light and the photodetection unit to start the generation of the detection signal when the detecting signal is received, and
        the photodetection unit is configured to continuously generate the detection signal after the start of the generation of the detection signal and before the start of the calculation in the calculation unit, and the instruction unit is configured to determine the start of the calculation on the basis of the detection signal.

2. The concentration measurement apparatus according to claim 1, wherein the instruction unit is configured to determine the start of the calculation on the condition that the intensity of the incident light is within a predetermined range.

3. The concentration measurement apparatus according to claim 1, wherein the instruction unit is configured to determine the start of the calculation on the condition that a state in which the intensity of the incident light is within a predetermined range continues for a predetermined period.

4. The concentration measurement apparatus according to claim 1, wherein the photodetection unit comprises a first photodetector separated from the light source by a first distance and a second photodetector separated from the light source by a second distance longer than the first distance, and
    the instruction unit is configured to determine the start of the calculation on the basis of the intensity of the incident light on the second photodetector.

5. A concentration measurement method of measuring a hemoglobin concentration-related numerical value in a head, with a probe attached thereto, which varies due to repetition of chest compression, the probe comprising a light source configured to output measurement light and a photodetection unit configured to generate a detection signal according to an intensity of incident light, the concentration measurement method comprising:
    detecting a connection of a controller and the probe and outputting a detecting signal, the controller comprising a calculation unit and an instruction unit;
    starting the output of the measurement light from the light source and the generation of the detection signal in the photodetection unit when the instruction unit receives the detecting signal;
    continuously generating the detection signal in the photodetection unit after the start of the generation of the detection signal;
    determining, by the instruction unit, a start of a calculation of the hemoglobin concentration-related numerical value in the head which varies due to the repetition of chest compression on the basis of the detection signal;
    outputting the measurement light from the light source; and performing, by the calculation unit, the calculation of the hemoglobin concentration-related numerical value on the basis of the detection signal according to the intensity of the measurement light propagated through the inside of the head.

6. The concentration measurement method according to claim 5, wherein in the determining the start of the calculation, the start of the calculation is determined on the condition that the intensity of the incident light is within a predetermined range.

7. The concentration measurement method according to claim 5, wherein in the determining the start of the calculation, the start of the calculation is determined on the condition that a state in which the intensity of the incident light is within a predetermined range continues for a predetermined period.

8. The concentration measurement method according to claim 5, wherein the photodetection unit comprises a first photodetector separated from the light source by a first distance and a second photodetector separated from the light source by a second distance longer than the first distance, and in the determining the start of the calculation, the start of the calculation is determined on the basis of the intensity of the incident light on the second photodetector.

* * * * *